United States Patent
Park (10) Patent No.: US 9,174,217 B2
(45) Date of Patent: Nov. 3, 2015

(54) DEVICE AND METHOD OF AMPLIFYING NUCLEIC ACIDS BY USING OIL LAYER COMPRISING EXOTHERMAL PARTICLES

(75) Inventor: Jong-myeon Park, Incheon (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 19 days.

(21) Appl. No.: 13/607,304

(22) Filed: Sep. 7, 2012

(65) Prior Publication Data

US 2013/0149746 A1  Jun. 13, 2013

(30) Foreign Application Priority Data

Dec. 9, 2011 (KR) .................. 10-2011-0132129

(51) Int. Cl.
| | | |
|---|---|---|
| *C12Q 1/68* | (2006.01) | |
| *C12M 1/42* | (2006.01) | |
| *B01L 7/00* | (2006.01) | |
| *C12P 19/34* | (2006.01) | |

(52) U.S. Cl.
CPC . *B01L 7/52* (2013.01); *C12P 19/34* (2013.01); *C12Q 1/6851* (2013.01); *B01L 7/00* (2013.01); *B01L 2200/0647* (2013.01); *B01L 2200/0673* (2013.01); *B01L 2300/1861* (2013.01); *B01L 2400/043* (2013.01)

(58) Field of Classification Search
None
See application file for complete search history.

(56) References Cited

U.S. PATENT DOCUMENTS

| 7,927,797 B2 | 4/2011 | Nobile et al. |
|---|---|---|
| 2005/0079510 A1 | 4/2005 | Berka et al. |
| 2009/0179171 A1* | 7/2009 | Sailor et al. ............ 252/62.51 R |
| 2010/0190153 A1 | 7/2010 | Diehl et al. |

FOREIGN PATENT DOCUMENTS

JP   2008-245612 A   10/2008

OTHER PUBLICATIONS

Bernath et al. In vitro compartmentalization by double emulsions: sorting and gene enrichment by fluorescence activated cell sorting. Analytical Biochemistry 2004;325:151-7.*
Mazutis et al. (Anal Chem, 2009, 81, p. 4813-4821).*
Veyret et al. (Journal of Magnetism and Magnetic Materials, 2005, vol. 295, p. 155-163).*
Miller et al. (Nature Methods, 2006, 3(7):561-570).*
Griffiths et al., Miniaturising the laboratory in emulsion droplets, *Trends in Biotechnology*, 24(9): 395-402 (2006).
Shah et al., Designer emulsions using microfluidics, *Materials Today*, 11(4):18-27 (2008).

* cited by examiner

*Primary Examiner* — Stephanie K Mummert
(74) *Attorney, Agent, or Firm* — Leydig, Voit & Mayer, Ltd.

(57) ABSTRACT

The disclosure describes example devices and methods for amplifying nucleic acids by using an oil layer including exothermal particles, forming an emulsion using the oil layer including exothermal particles, and performing a nucleic acids amplification reaction in the emulsion. The nucleic acids amplification reaction may be effectively performed even with a small amount of a sample by maximizing nucleic acids amplification efficiency, reducing reaction time, and improving controls to be convenient.

9 Claims, 7 Drawing Sheets

DEVICE AND METHOD OF AMPLIFYING NUCLEIC ACIDS BY USING OIL LAYER COMPRISING EXOTHERMAL PARTICLES

CROSS-REFERENCE TO RELATED APPLICATIONS

This application claims the benefit of Korean Patent Application No. 10-2011-0132129, filed on Dec. 9, 2011, in the Korean Intellectual Property Office, the disclosure of which is incorporated herein in its entirety by reference.

BACKGROUND

A nucleic acid amplification reaction is a technique for sequentially amplifying a region of nucleic acids (including specific nucleotide sequences, a so-called target site) by repeatedly heating and cooling a sample (including the nucleic acids) to exponentially amplify the nucleic acids including the target site. Nucleic acid amplification reactions are widely used in areas such as biotechnology, genetic engineering, and medical fields. For example, polymerase chain reaction (PCR) is a technique for exponentially amplifying deoxyribonucleic acids (DNAs) including the specific nucleotide sequences by repeatedly (1) denaturing a sample including double-stranded DNAs by heating the sample to a temperature of about 95° C. to isolate the double-stranded DNAs to single-stranded DNAs; (2) providing forward and reverse oligonucleotide primers, which include sequences complementary to the specific nucleotide sequences about to be amplified, to the sample after denaturing; (3) annealing to form a partial DNA-primer complex binding the primers to the specific nucleotide sequences of the single-stranded DNAs by cooling the primers and the denatured single-stranded DNAs to a temperature of about 55° C. and (4) extension synthesizing double stranded DNAs based on primers of the partial DNA-primer complex by the DNA polymerase (e.g., Tag polymerase) while maintaining a temperature of the sample at about 72° C. after the annealing.

Since a nucleic acid amplification reaction is a procedure preceded or premised in most fields of its application, the nucleic acid amplification reaction needs to be proceeded accurately and rapidly. Therefore, various nucleic acid amplification techniques, which may derive reliable nucleic acid amplification results with a small amount of sample and may reduce reaction time, have recently been introduced. Moreover, nucleic acid amplification devices for easily performing the nucleic acid amplification reaction by controlling various samples and reagents in a single instrument are currently being developed.

SUMMARY

Provided are a device and a method of forming an emulsion by using an oil layer and effectively performing a nucleic acids amplification reaction in the emulsion.

Additional aspects will be set forth in part in the description which follows and, in part, will be apparent from the description, or may be learned by practice of the presented embodiments.

According to an aspect of the present invention, a device for amplifying nucleic acids includes a reaction vessel, and the vessel includes a first aqueous solution including template nucleic acids including a target site to be amplified and a reagent for amplifying the target site; an oil layer surrounding the first aqueous solution to be sealed and including exothermal particles; and a second aqueous solution surrounding the oil layer.

The nucleic acids amplification device may further include a heat supply means heating the exothermal particles.

The exothermal particles may be metal particles.

The metal particles may be iron oxide particles.

The nucleic acids amplification device may further include a magnetic force supply means supplying magnetic force to the metal particles.

The reaction vessel may be made of a light-transmitting material, and the nucleic acids amplification device may further include a heat supply means heating the exothermal particles in non-contact way.

The non-contact heat supply means may provide electromagnetic waves, a laser, or infrared rays.

According to another aspect of the present invention, a method of amplifying nucleic acids, and the method may include mixing the template nucleic acids including a target site to be amplified, a first aqueous solution including a reagent for amplifying the target site, and an oil including exothermal particles; forming a first emulsion of which the oil surrounds the first aqueous solution; forming a second emulsion of which a second aqueous solution surrounds the first emulsion by adding the second aqueous solution to the first emulsion; and performing nucleic acids amplification reaction by heating the exothermal particles.

The method of amplifying nucleic acids, after performing the nucleic acids amplification reaction, may further include isolating the first emulsion from the second emulsion; and isolating nucleic acids amplification product from the first emulsion.

The exothermal particles may be metal particles.

The metal particles may be iron oxide particles.

The reaction vessel may be made of a light-transmitting material while the method may further include heating the exothermal particles in non-contact way.

The heating in non-contact way is heating by supplying electromagnetic waves, a laser, or infrared rays to the exothermal particles.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like components throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Figure 1:
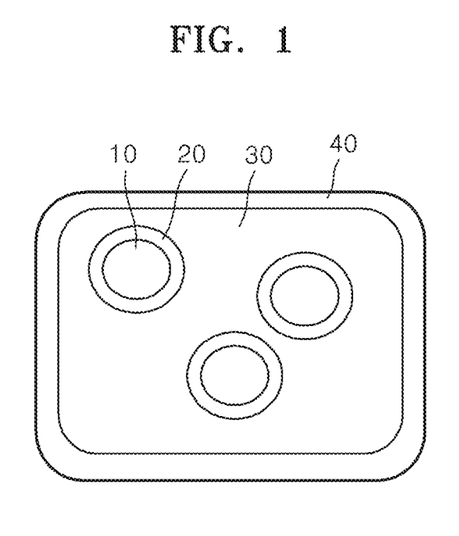
FIG. 1 illustrates an example reaction vessel having certain components, which may be included in a nucleic acid amplification device.

FIG. 1 illustrates an example embodiment of a reaction vessel 40, having components 10, 20, and 30, which may be included in a nucleic acid amplification device according to an embodiment.

The nucleic acid amplification device of FIG. 1 includes the reaction vessel 40 for a nucleic acid amplification reaction. The nucleic acid amplification device may include, as well as the reaction vessel 40, other modules necessary for the nucleic acid amplification reaction. Examples of other modules include, but are not limited to, a heating unit, a cooling unit, a sample storage chamber providing a sample for the nucleic acid amplification, and a waste chamber to store waste after the nucleic acid amplification reaction. These other modules may be disposed along with the reaction vessel 40 for operation of the nucleic acid amplification reaction. The nucleic acid amplification device may include a body shaped in the form of disc or disk controlling a flow of fluid by using centrifugal force and centripetal force. In some embodiments a plurality of channels and valves are disposed in the body, and the reaction vessel 40 is disposed in the body and connected to the plurality of channels and valves for fluid to flow. Also, a heat providing unit 50, a magnetic force providing unit 60, and the like, which are described in detail hereinafter, may be drivingly disposed with the reaction vessel 40.

Referring to FIG. 1, the reaction vessel 40 includes a first aqueous solution 10, an oil layer 20, and a second aqueous solution 30.

The first aqueous solution 10 includes template nucleic acids including a target site to be amplified and a reagent for amplifying the target site. The template nucleic acids include the target site (specified to nucleotide sequences), which is to be amplified. The target site may include a specific gene, for example, a causative gene of diseases such as cancer, tuberculosis, allergy, or the like. The template nucleic acids may include all types of amplifiable nucleic acids, for example, may be deoxyribonucleic acids (DNA), ribonucleic acid (RNA), peptide nucleic acid (PNA), or locked nucleic acid (LNA). The reagent includes all types of reagents used for amplification of the target site included in the template nucleic acids. For example, the reagent may include forward primer, reverse primer, dNTPs (dATP, dCTP, dGTP, and dTTP), nucleic acid polymerase (Tag polymerase), buffer, or the like in a polymerase chain reaction (PCR).

Figure 2A:
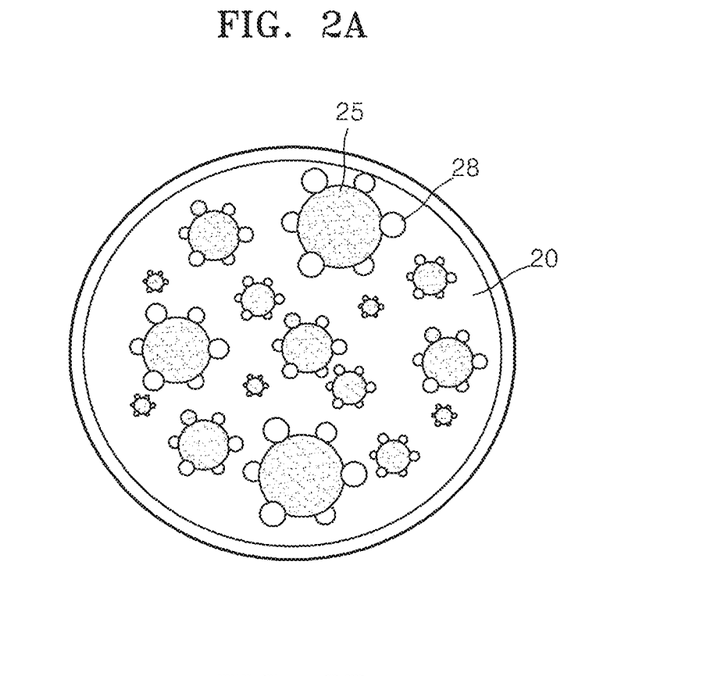
FIGS. 2A through 2B illustrate components included in an oil layer included in an example reaction vessel.
Figure 2B:
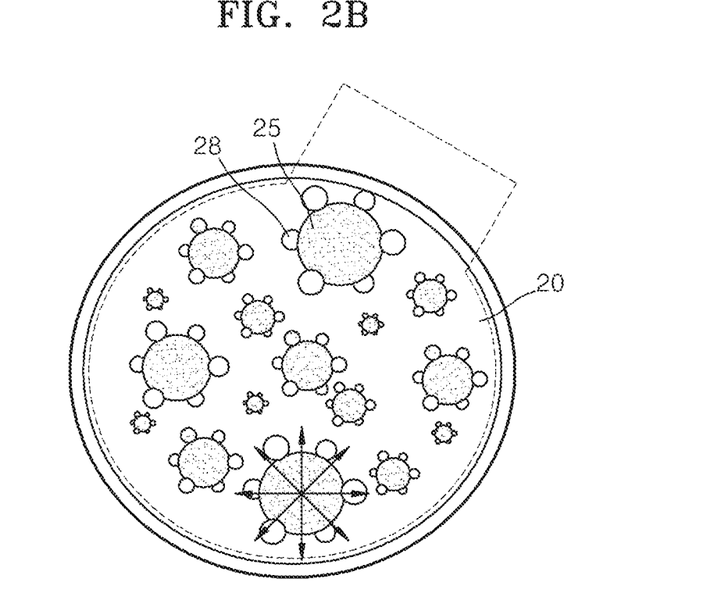

FIGS. 2A through 2B illustrate example components included in the oil layer 20. The oil layer 20 includes oil. The oil is present in a liquid state at room temperature and is a material that spreads and forms a layer on a water surface when mixed with an aqueous solution since the oil is lighter than water. The oil may include all types of materials which have viscosity, combustibility, and insolubility. Examples of the oil are hydrocarbon oil and mineral oil. The oil layer 20 surrounds a surface of the first aqueous solution 10 and thus seals the first aqueous solution 10 not to be released through the oil layer 20. The structure of the oil layer 20 and the first aqueous solution 10 surrounded by the oil layer 20 is referred to as water-in-oil emulsion (W/O emulsion). Thus, the template nucleic acids and the reagent included in the first aqueous solution 10 may be used in the nucleic acid amplification reaction in the oil layer 20.

The oil layer 20 of FIGS. 2A through 2B includes exothermal particles 25. Referring to FIG. 2A, the exothermal particles 25 may be all types of material capable of heat release with energy supplied autonomously or extraneously, for example, metal nanoparticles, magnetic beads, more particularly, iron oxide ($Fe_2O_3$ or $Fe_3O_4$) particles, but are not limited thereto. Also, the exothermal particles 25 may be treated with a surfactant 28 on their surfaces, which may increase an exothermal effect by reducing surface tension of contact surfaces between the exothermal particles and the oil 20. Referring to FIG. 2B, the exothermal particles 25 may rapidly transfer heat toward all directions around the exothermal particles 25 by being rapidly heated by, e.g., laser irradiation. Accordingly, the first aqueous solution 10 surrounded by the oil layer 20 may receive heat in a sealed space.

The second aqueous solution 30 is a solution of which a solvent is water and also includes distilled water. The second aqueous solution 30 surrounds the oil layer 20. The structure of the first aqueous solution 10, the oil layer 20 surrounding the first aqueous solution 10, and the second aqueous solution 30 surrounding the oil layer 20 is referred to as water-in-oil-in-water emulsion (W/O/W emulsion). The second aqueous solution 30 may include a material with a higher heat capacity than the oil layer 20. Thus, when the exothermal particles 25 are heated, while a temperature of the first aqueous solution 10 in the sealed space of the oil layer 20 increases rapidly due to a heat capacity difference between the oil layer 20 and the second aqueous solution 30, a temperature of the second aqueous solution 30 with a higher heat capacity than that of the oil layer 20 increases relatively little. Thus, according to an embodiment, the nucleic acid amplification efficiency and time for the target site may be considerably improved since the exothermal particles 25 enable rapidly heating the first aqueous solution 10 with a small amount of heat supply.

Figure 3:
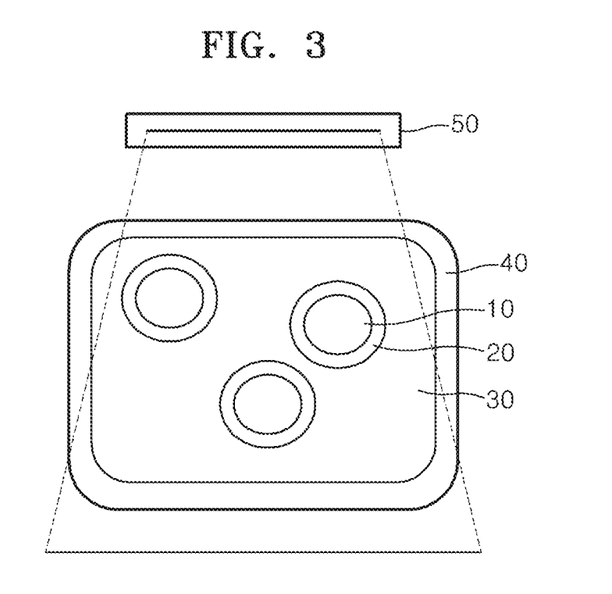
FIG. 3 illustrates an example reaction vessel and heat supply unit, which may be included in the nucleic acid amplification device.

FIG. 3 illustrates an example reaction vessel 40 and a heat supply unit 50, which may be included in a nucleic acid amplification device according to an embodiment.

The nucleic acid amplification device according to an embodiment includes the reaction vessel 40 and the heat supply unit 50 for heating the exothermal particles 25. The heat supply unit 50 may be anything that supplies heat to the exothermal particles 25. Referring to FIG. 3, the heat supply unit 50 may be a non-contact heating unit, for example, electromagnetic waves, laser emission, or infrared ray supply means, and if so, the reaction vessel 40 only needs to be made of a light-emitting material irrelevant to heat conductivity. For example, an electromagnetic waves supply unit may supply the electromagnetic waves toward the reaction vessel 40, the electromagnetic waves supply heat to the second aqueous solution 30, the oil layer 20, and the first aqueous solution 10 by transmitting through the reaction vessel 40 made of the light-transmitting material, and the exothermal particles 25 among them are the most rapidly heated. Accordingly, the first aqueous solution 10 surrounded by the oil layer 20 is heated much faster than the second aqueous solution 30 since the second aqueous solution 20 has higher heat capacity and is distributed in a wider area than the first aqueous solution 10. However, in this example, when the electromagnetic waves supply unit stops supplying the electromagnetic waves, the exothermal particles 25 are the most rapidly cooled. Accordingly, the first aqueous solution 10 surrounded by the oil layer 20 is cooled much faster than the second aqueous solution 30 since the second aqueous solution 20 has higher heat capacity and is distributed in a wider area than the first aqueous solution 10. Thus, according to an embodiment, the nucleic acid amplification reaction may be rapidly preceded in the first aqueous solution 10.

Figure 4:
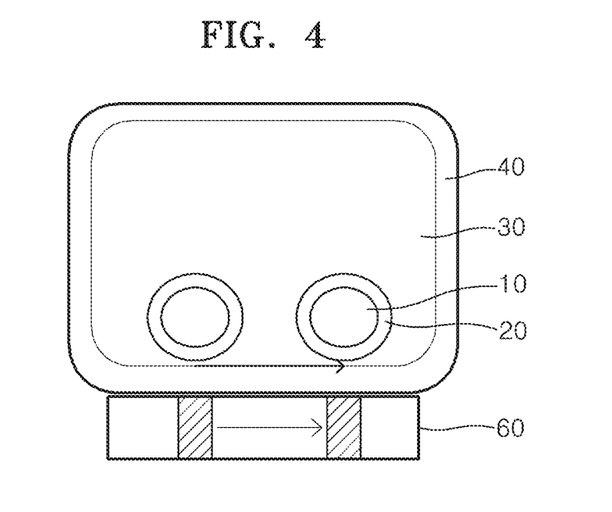
FIG. 4 illustrates an example reaction vessel and a magnetic force supply unit, which may be included in the nucleic acid amplification device.

FIG. 4 illustrates an example reaction vessel 40 and a magnetic force supply unit 60, which may be included in a nucleic acid amplification device according to an embodiment.

The nucleic acid amplification device of the example embodiment depicted by FIG. 4 includes the reaction vessel 40 and the magnetic force supply unit 60 for supplying magnetic force to metal particles as the exothermal particles. The magnetic force supply unit 60 is for controlling transfer of a complex of the first aqueous solution 10 and the oil layer 20 in the second aqueous solution 30 of the reaction vessel 40 by supplying magnetic force to the metal particles. Examples of the magnetic force supply unit 60 include, but are not limited to, a permanent magnet, an electromagnet, or the like.

Referring to FIG. 4, the reaction vessel 40 is disposed to receive the magnetic force from the magnetic force supply unit 60, and the magnetic force supply unit 60 may be made in various types of contact or non-contact forms for the reaction vessel 40. Hatched patterned portions in the magnetic force supply unit 60 may be a permanent magnet or an electromagnet, and transfer (in the arrow direction) of the complex of the first aqueous solution 10 and the oil layer 20 may be controlled by transfer (in the arrow direction) of the hatched patterned portions. As a result, the magnetic force supply unit 60 may freely control a position of the complex in various two or more chambers and/or channels included in the nucleic acid amplification device.

Figure 5:
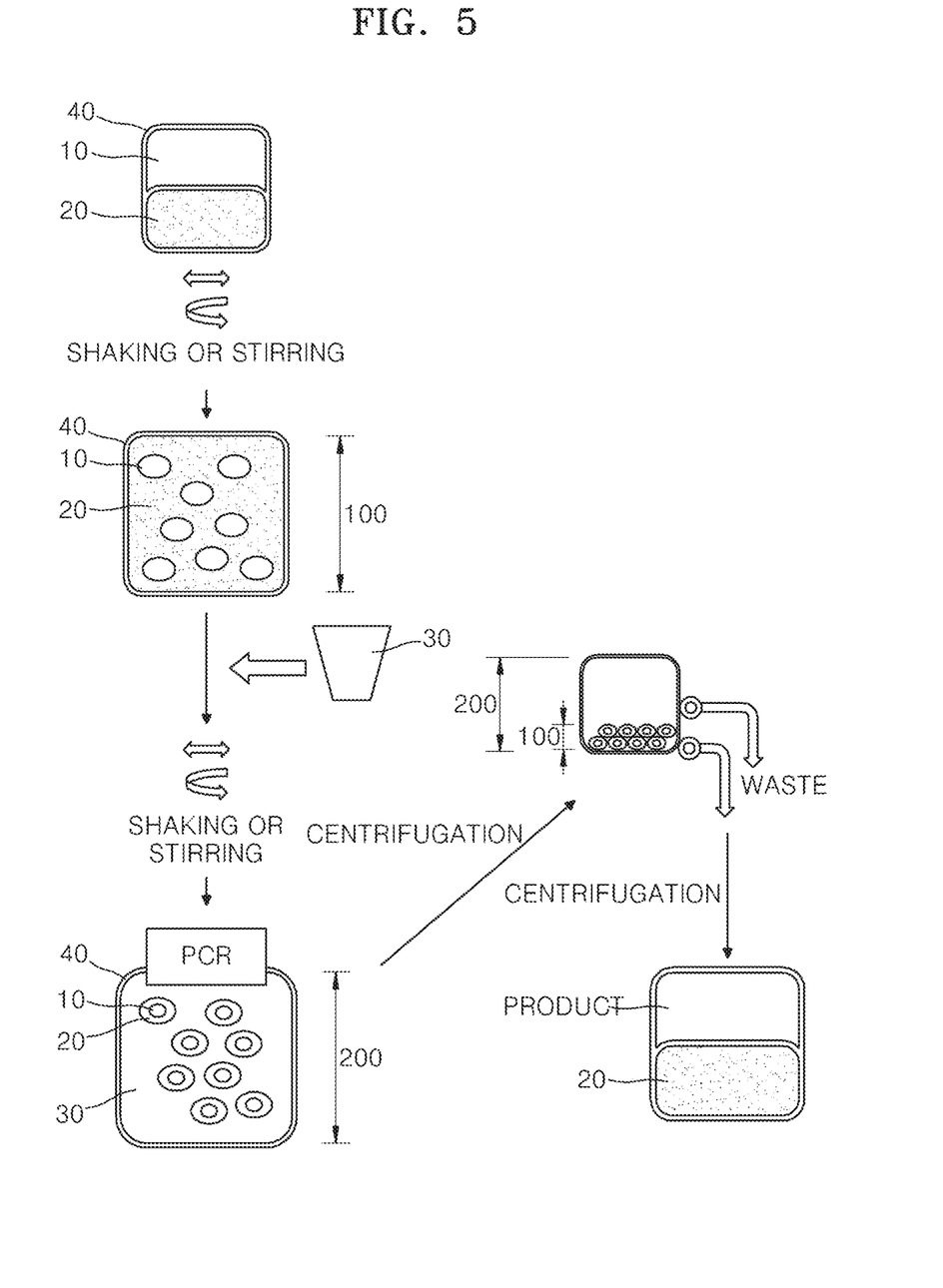
FIG. 5 illustrates a series of steps to perform a method of amplifying nucleic acids.

FIG. 5 illustrates an example method for amplifying nucleic acids. In the method for amplifying nucleic acids of FIG. 5, a first aqueous solution 10, exothermal particles, oil or an oil layer 20, and a second aqueous solution 30 are as described above.

Referring to FIG. 5, the method for amplifying nucleic acids includes mixing template nucleic acids including a target site to be amplified, the first aqueous solution 10 including a reagent for amplifying the target site, and the oil 20 including the exothermal particles. Here, the first aqueous solution 10 and the oil 20 including the exothermal particles do not dissolve with each other, and form a border and layers that are vertically separated.

Also, the method for amplifying nucleic acids according to another embodiment includes forming a first emulsion 100 of which the oil 20 surrounds the first aqueous solution 10. Here, the first emulsion 100 may be formed as two or more water-in-oil emulsions (W/O emulsions) in the reaction vessel 40.

Also, the method for amplifying nucleic acids, according to an embodiment, includes forming a second emulsion 200 of which the second aqueous solution 30 surrounds the first emulsion 100 by adding the second aqueous solution 30 into the first emulsion 100. Here, the second emulsion 200 may be formed as two or more water-in-oil-in-water emulsions (W/O/W emulsions) in the reaction vessel 40.

Also, the method for amplifying nucleic acids, according to an embodiment, includes performing the nucleic acid amplification reaction by heating the exothermal particles. Referring to FIG. 5, the nucleic acid amplification reaction may be a polymerase chain reaction (PCR). Performing the nucleic acid amplification reaction by heating the exothermal particles includes controlling a temperature necessary for the PCR, for example, about 95° C. in a denaturing step, about 55° C. in an annealing step, and about 72. ° C. in an extension step by supplying or blocking heat to the exothermal particles. Here, the exothermal particles may be metal particles, more particularly, iron oxides ($Fe_2O_3$ or $Fe_3O_4$), the reaction vessel 40 is made of a light-transmitting material, and heating the exothermal particles in non-contact way may be further included. The exothermal particles may be heated by, e.g., electromagnetic waves, a laser, infrared rays supply, or the like.

Also, referring to the example embodiment of FIG. 5, the method for amplifying nucleic acids may further include isolating the first emulsion 100 from the second emulsion 200 and isolating a nucleic acid amplification product from the first emulsion 100. The isolating the first emulsion 100 from the second emulsion 200 and the isolating the nucleic acid amplification product from the first emulsion 100 may be performed by using centrifugation. The second emulsion 200 is formed as water-in-oil-in-water emulsion (W/O/W emulsion) including the first emulsion 100, which is a complex of the first aqueous solution 10 and the oil layer 20, and the second aqueous solution 30. However, because of a density difference between the first emulsion 100 and the second aqueous solution 30, the second aqueous solution 30, which is waste, is disposed in an upper layer and the first emulsion 100 in a lower layer when the second emulsion 200 is centrifuged, and thus the second aqueous solution 30 may be removed from the upper layer. Also, the first emulsion 100 is formed as water-in-oil emulsion (W/O emulsion) including the first aqueous solution 10 and the oil layer 20. However, because of a density difference between the first aqueous solution 10 and the oil layer 20, the first aqueous solution 10 is disposed in an upper layer and the oil layer 20 in a lower layer when the first emulsion 100 is centrifuged, and thus the first aqueous solution 10 may be isolated from the upper layer. Therefore, the nucleic acid amplification product included in the first aqueous solution 10 may be obtained.

Example

Figure 6:
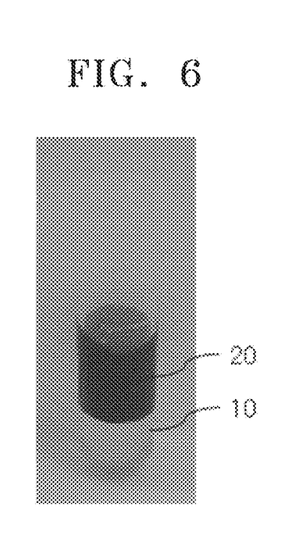
FIG. 6 is a photograph of an example oil including the first aqueous solution and the exothermal particles before mixing to form the first emulsion.
Figure 7:
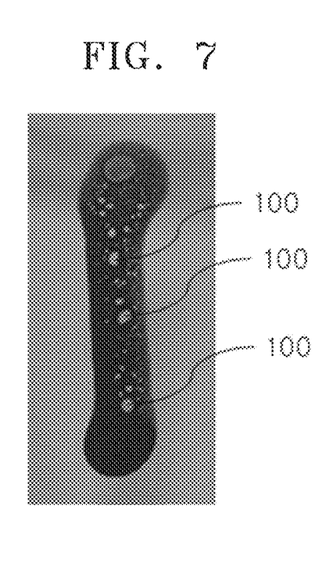
FIG. 7 is a photograph of an example oil including the first aqueous solution and the exothermal particles after forming a first emulsion by mixing.

About 500 μl of the first aqueous solution 10 including template nucleic acids including any target site, a reagent (i.e. forward primer, reverse primer, dNTPs(dATP, dCTP, dGTP, and dTTP), taq polymerase, a PCR buffer, and the like) for amplifying the target site is prepared, and the first aqueous solution 10 was put into a reaction vessel of a transparent glass material. Then, about 500 μl of the oil 20 including iron oxides ($Fe_2O_3/Fe_3O_4$) as the exothermal particles and a hydrocarbon oil was prepared and put into the reaction vessel. FIG. 6 is a photograph of the oil 20 including the first aqueous solution 10 and the exothermal particles before mixing according to another embodiment to form the first emulsion. Then, the first aqueous solution 10 and the oil 20 including the exothermal particles were mixed (e.g., by shaking or stirring) in the reaction vessel. FIG. 7 is a photograph of the oil 20 including the first aqueous solution 10 and the exothermal particles after forming the first emulsion 100 by mixing.

Figure 8:
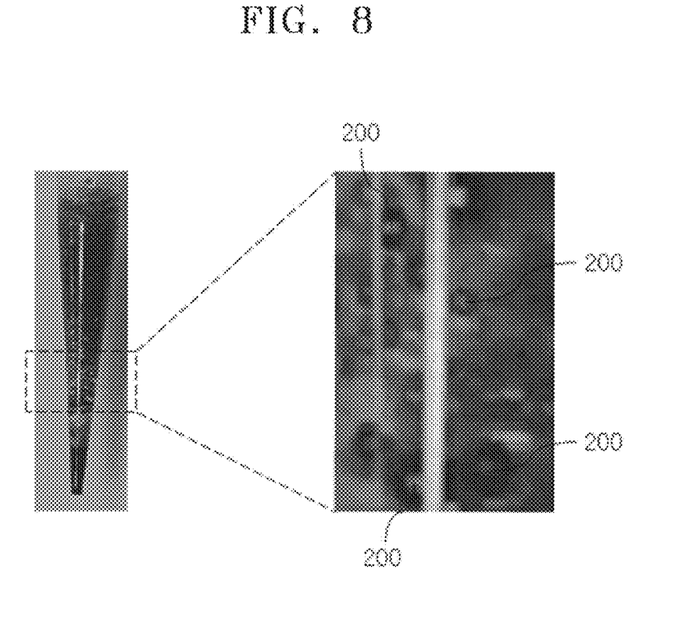
FIG. 8 is a photograph after a second emulsion is formed.

About 500 μl of distilled water was prepared as the second aqueous solution 30 and put into the reaction vessel, and the second aqueous solution 30 was mixed (e.g., by shaking or stirring) to form the second emulsion 200. FIG. 8 is a photograph after the second emulsion 200 is formed according to an embodiment, and another embodiment, and an enlarged photograph to illustrate the second emulsion 200 more clearly.

Figure 9:
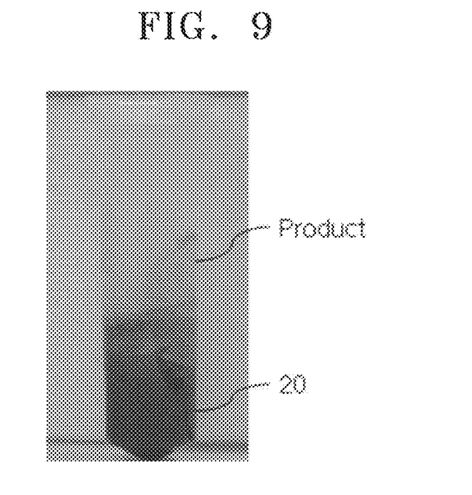
FIG. 9 is a photograph of the first aqueous solution product and the oil layer vertically stacked.
Figure 10:
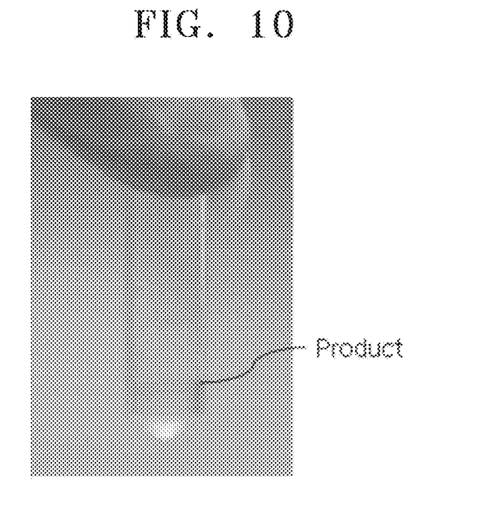
FIG. 10 is a photograph of the first aqueous solution product including the nucleic acid amplification product isolated from a stack of the first aqueous solution product and the oil layer with the same method in FIG. 9.

After the second emulsion 200 is formed, the second emulsion 200 was heated or cooled by repeatedly supplying or blocking electromagnetic waves to the reaction vessel of the transparent glass material, and thus about 20 cycles of the PCR involving about 95° C. of the denaturing step, about 55° C. of the annealing step, and about 72° C. of the extension step was performed. After completing the PCR, the second emulsion 200 was transferred to another vessel of a transparent glass material, and a first centrifugation was performed. After completing the first centrifugation, an upper layer solution (the second aqueous solution) was removed, and the first emulsion 100 collected in the lower layer was centrifuged to perform a second centrifugation. FIG. 9 is a photograph of the first aqueous solution product and the oil layer 20 vertically stacked. Next, an upper layer solution was isolated while the oil layer 20 collected in a lower layer remained. FIG. 10 is a photograph of the first aqueous solution product including the nucleic acids amplification product isolated from a stack of the first aqueous solution product and the oil layer 20 with the same method in FIG. 9. Then, as a result of a get electrophoresis assay performed on the isolated first aqueous solution, the target site amplified in the template nucleic acids is confirmed.

As described above, by forming an emulsion using an oil layer including exothermal particles and performing a nucleic acids amplification reaction in the emulsion according to the one or more of the above embodiments, a nucleic acid amplification reaction may be effectively performed even with a small amount of a sample by maximizing a nucleic acid amplification efficiency, reducing a reaction time, and improving controls to be convenient.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A device for amplifying nucleic acids comprising:
    a reaction vessel, wherein the vessel comprises a first aqueous solution comprising template nucleic acids each of which comprises a target site to be amplified and a reagent for amplifying the target site;
    an oil layer surrounding and sealing the first aqueous solution, wherein the oil layer comprises exothermal particles consisting of iron oxide and, optionally, a surfactant; and
    a second aqueous solution surrounding the oil layer.

2. The device of claim 1, further comprising a heat supply unit for heating the exothermal particles.

3. The device of claim 1, further comprising a magnetic force supply unit for supplying magnetic force to the exothermal particles.

4. The device of claim 1, further comprising a heat supply unit for non-contact heating of the exothermal particles, wherein the reaction vessel comprises a light-transmitting material.

5. The device of claim 4, wherein the heat supply unit provides non-contact heating by at least one of electromagnetic waves, laser emission, and infrared rays.

6. A method of amplifying nucleic acids, the method comprising:
    mixing template nucleic acids comprising a target site to be amplified, a first aqueous solution comprising a reagent for amplifying the target site, and an oil, wherein the oil comprises exothermal particles consisting of iron oxide and, optionally, a surfactant;
    forming a first emulsion in which the oil surrounds the first aqueous solution;
    forming a second emulsion in which a second aqueous solution surrounds the first emulsion by adding the second aqueous solution to the first emulsion; and
    performing a nucleic acid amplification reaction by heating the exothermal particles.

7. The method of claim 6 further comprising, after performing the nucleic acid amplification reaction:
    isolating the first emulsion from the second emulsion; and
    isolating a nucleic acid amplification product from the first emulsion.

8. The method of claim 6, further comprising non-contact heating of the exothermal particles, wherein the reaction vessel comprises a light-transmitting material.

9. The method of claim 8, wherein the non-contact heating is supplied by one of electromagnetic waves, laser emission, and infrared rays to the exothermal particles.

* * * * *